United States Patent
Chen et al.

(10) Patent No.: US 11,795,437 B2
(45) Date of Patent: Oct. 24, 2023

(54) METHOD FOR CULTIVATING PRIMARY HUMAN PULMONARY ALVEOLAR EPITHELIAL CELLS AND APPLICATION THEREOF

(71) Applicant: National Yang Ming Chiao Tung University, Hsinchu (TW)

(72) Inventors: Guan-Yu Chen, Hsinchu County (TW); Jia-Wei Yang, Taoyuan (TW)

(73) Assignee: NATIONAL YANG MING CHIAO TUNG UNIVERSITY, Hsinchu (TW)

( * ) Notice: Subject to any disclaimer, the term of this patent is extended or adjusted under 35 U.S.C. 154(b) by 0 days.

(21) Appl. No.: 17/497,409

(22) Filed: Oct. 8, 2021

(65) Prior Publication Data

US 2022/0372445 A1    Nov. 24, 2022

(30) Foreign Application Priority Data

May 20, 2021    (TW) .................. 110118300

(51) Int. Cl.
*C12N 5/071*    (2010.01)
(52) U.S. Cl.
CPC ...... *C12N 5/0688* (2013.01); *C12N 2501/117* (2013.01); *C12N 2501/119* (2013.01); *C12N 2501/15* (2013.01); *C12N 2501/42* (2013.01); *C12N 2501/727* (2013.01); *C12N 2513/00* (2013.01); *C12N 2533/52* (2013.01); *C12N 2533/54* (2013.01)
(58) Field of Classification Search
None
See application file for complete search history.

(56) References Cited

FOREIGN PATENT DOCUMENTS

| WO | WO-2014/052458 A1 | 4/2014 |
| WO | WO-2016/143803 A1 | 9/2016 |
| WO | WO-2019/153004 A1 | 8/2019 |

OTHER PUBLICATIONS

Van Riet et al. In vitro modelling of alveolar repair at the air-liquid interface using alveolar epithelial cells derived from human induced pluripotent stem cells. Sci Rep 10, 5499 (2020). (Year: 2020).*
Shiraishi et al "In Vitro Expansion of Endogenous Human Alveolar Epithelial Type II Cells in Fibroblast-Free Spheroid Culture" Biochemical and Biophysical Research Communications vol. 515, pp. 579-585, 2019.
Shiraishi et al "Mesenchymal-Epithelial Interactome Analysis Reveals Essential Factors Required for Fibroblast-Free Alveolosphere Formation" iScience vol. 11, pp. 318-333, 2019.

* cited by examiner

*Primary Examiner* — Allison M Fox
*Assistant Examiner* — Alyssa G Weston
(74) *Attorney, Agent, or Firm* — Morse, Barnes-Brown & Pendleton, P.C.; Martin Zhang, Esq.

(57) ABSTRACT

Disclosed herein is a method for cultivating primary human pulmonary alveolar epithelial cells (HPAEpiC), which includes cultivating the primary HPAEpiC in a first medium containing a basal medium, a culture supplement, and a Rho kinase inhibitor, and a second medium containing the basal medium and the culture supplement in sequence. The culture supplement includes Jagged-1 (JAG-1) peptide, human Noggin protein, transforming growth factor-β (TGF-β) type I receptor inhibitor SB431542, human fibroblast growth factor 7 (hFGF-7), hFGF-10, and glycogen synthase kinase 3 (GSK-3) inhibitor CHIR99021. Also disclosed is a method for preparing a three-dimensional cell culture of alveolar epithelium using the first medium and the second medium.

3 Claims, 13 Drawing Sheets
(9 of 13 Drawing Sheet(s) Filed in Color)

| 18th day of submerged cultivation | 8th day of air-liquid interface cultivation | 15th day of air-liquid interface cultivation |

| Infection with SARS-CoV-2 pseudovirus (m.o.i) | – | 1 | 10 | 20 |
| --- | --- | --- | --- | --- |
| | Comparative group | Experimental group 1 | Experimental group 2 | Experimental group 3 |

FIG. 9

METHOD FOR CULTIVATING PRIMARY HUMAN PULMONARY ALVEOLAR EPITHELIAL CELLS AND APPLICATION THEREOF

CROSS-REFERENCE TO RELATED APPLICATION

This application claims priority of Taiwanese Invention Patent Application No. 110118300, filed on May 20, 2021.

FIELD

The present disclosure relates to a method for cultivating primary human pulmonary alveolar epithelial cells. The present disclosure also relates to a method for preparing a three-dimensional cell culture of alveolar epithelium.

BACKGROUND

Human pulmonary alveolar epithelium is mainly composed of alveolar type 1 epithelial cells (AT1 cells) and alveolar type 2 epithelial cells (AT2 cells), and tissues formed by tight junctions and adherens junctions between the AT1 cells and the AT2 cells, providing important epithelial barrier function. The AT1 cells account for about 8% of the total number of lung cells, are squamous, thin and flat epithelial lining cells which cover more than 95% of the alveolar surface to form main structure of the alveoli, and are involved in gas exchange between the gas in the alveoli and the blood in the surrounding capillaries. The AT2 cells account for about 16% of the total number of lung cells, are cuboidal and smaller that the AT1 cells, and are scattered among the AT1 cells, covering only 5% of the alveolar surface. In addition to synthesizing and secreting pulmonary surfactant proteins for maintaining structural stability of the alveoli, the AT2 cells also serve as the stem cells of the pulmonary alveolar epithelium, i.e., the AT2 cells are capable of undergoing cellular division and differentiation to produce new AT1 cells so as to repair damaged lung tissues.

At present, most of the research related to various aspects of the pulmonary alveolar epithelium (e.g., disease progression and treatment, drug screening, etc.) utilizes AT2 cells derived from immortalized human lung adenocarcinoma cell lines, such as A549 or NCI-441, or human induced pluripotent stem cells (hiPSC) as in vitro models of pulmonary alveolar epithelium. However, differences exist between these in vitro models and real human tissues in terms of physiological functions and gene expression. In particular, hiPSC-derived AT2 cells lack complete pulmonary alveolar epithelium function due to absence of AT1 cells.

As reported in Wang H. Y. et al. (2018), *BMC Cell Biol.*, 19(1):10, primary swine tracheal epithelial cells (STECs) and immortalized STECs were subjected to air-liquid interface cultivation which mimics the environment of human pulmonary alveolar epithelium, so as to determine the differences of differentiation capability and immunological functions between these cells. The results show that, in comparison with the immortalized STECs, the formation of tight junctions in the primary STECs is more complete and the duration of cilia expression is longer, indicating that use of primary epithelial cells is an ideal way for establishing an in vitro respiratory tract epithelial cell model. Therefore, in order to establish an in vitro model of pulmonary alveolar epithelium that is more representative of the real physiological condition in the pulmonary alveolar epithelium of the human body, researchers have endeavored to isolate primary human pulmonary alveolar epithelial cells (primary HPAEpiC) from tissues or organs of healthy donors for cultivation.

Studies related to the cultivation of primary HPAEpiC have found that fibroblasts can provide an alveolar stem cell niche to support the growth of AT2 cells, and thus, in vitro cultivation of primary HPAEpiC is usually performed by co-cultivation of primary HPAEpiC with human fibroblasts. However, such co-cultivation not only involves complicated steps, but also might cause interference during subsequent analysis procedures.

As reported in Shiraishi K. et al. (2019), Biochem. Biophys. Res. Commun., 515(4):579-585, commercially available primary HPAEpiC was mixed with a commercially available small airway epithelial growth medium containing various growth factors and matrix solubilized basement membrane matrix secreted by Engelbreth-Holm-Swarm (EHS) mouse sarcoma cells ("MATRIGEL®"), followed by cultivation in an epithelial cell culture medium supplemented with various signal ligands and inhibitors after the MATRIGEL® had solidified, so as to determine in vitro expansion of endogenous human AT2 cells. The result shows that the AT2 cells were able to proliferate in vitro, and were capable of forming spheroids. Thereafter, a magnetic-activated cell sorting system was further utilized to separate the spheroids formed by the AT2 cells, so as to avoid interference from basal cells and other cells present in the primary HPAEpiC. However, such cultivation method only demonstrates formation of AT2 spheroids in a three-dimensional cell culture system, and is not applicable to the air-liquid interface cultivation that simulates the environment of human pulmonary alveolar epithelium.

SUMMARY

Therefore, an object of the present disclosure is to provide a method for cultivating primary human pulmonary alveolar epithelial cells, which can alleviate at least one of the drawbacks of the prior art, and which includes:

cultivating the primary human pulmonary alveolar epithelial cells in a first medium that includes a basal medium, a culture supplement, and a Rho kinase inhibitor, so as to obtain cultured primary human pulmonary alveolar epithelial cells; and cultivating the cultured primary human pulmonary alveolar epithelial cells in a second medium that includes the basal medium and the culture supplement, so as to obtain proliferated primary human pulmonary alveolar epithelial cells.

The culture supplement includes Jagged-1 (JAG-1) peptide, human Noggin protein (hNoggin) protein, transforming growth factor-β (TGF-β) type I receptor inhibitor SB431542, human fibroblast growth factor 7 (hFGF-7), human fibroblast growth factor 10 (hFGF-10), and glycogen synthase kinase 3 (GSK-3) inhibitor CHIR99021.

Another object of the present disclosure is to provide a method for preparing a three-dimensional cell culture of alveolar epithelium, which can alleviate at least one of the drawbacks of the prior art, and which includes:

subjecting primary human pulmonary alveolar epithelial cells to submerged cultivation in a first medium that includes a basal medium, a culture supplement, and a Rho kinase inhibitor, so as to obtain cultured primary human pulmonary alveolar epithelial cells;

subjecting the cultured primary human pulmonary alveolar epithelial cells to submerged cultivation in a second medium that includes the basal medium and the culture supplement, so as to obtain proliferated primary human pulmonary alveolar epithelial cells; and subjecting the proliferated primary human pulmonary alveolar epithelial cells to air-liquid interface cultivation in the second medium, so as to obtain the three-dimensional cell culture of alveolar epithelium.

The culture supplement includes JAG-1 peptide, hNoggin protein, SB431542, hFGF-7, hFGF-10, and CHIR99021.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Other features and advantages of the present disclosure will become apparent in the following detailed description of the embodiments with reference to the accompanying drawings, of which:

FIG. 9 shows the result of immunofluorescence staining assay for detection of HT1-56 and HT2-280 proteins (i.e., markers of AT1 cells and AT2 cells, respectively), and for detecting the presence of severe acute respiratory syndrome coronavirus 2 (SARS-CoV-2) pseudovirus in the 3D cell cultures of alveolar epithelium of the comparative group and experimental groups 1 to 3 of Example 3, infra, in which the AT1 cells, AT2 cells, SARS-CoV-2 pseudovirus and cell nuclei were respectively represented by red, purple, green and blue fluorescence;

DETAILED DESCRIPTION

Figure 1:
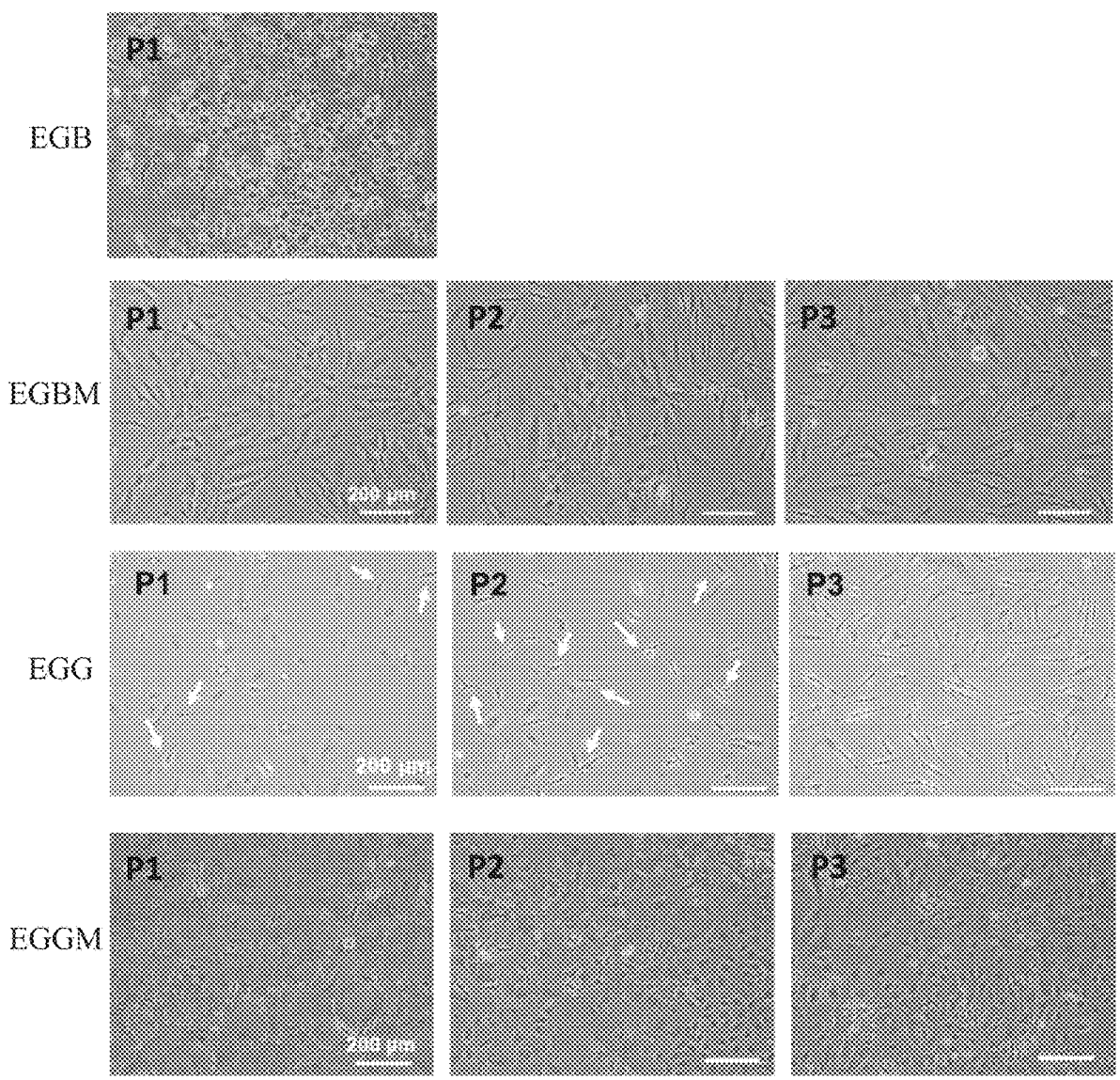
FIG. 1 shows light microscopy images of P1 cells, P2 cells and P3 cells cultured from primary human pulmonary alveolar epithelial cells (primary HPAEpiC) in the experimental group B (EGB), experimental group BM (EGBM), experimental group G (EGG) and experimental group GM (EGGM) of Example 1, infra, in which the arrows point to slender, spindle-shaped cells.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

In the development of methods for cultivating primary human pulmonary alveolar epithelial cells (primary HPAEpiC), the applicant surprisingly found that use of a basal medium, a culture supplement containing a combination of specific components, and a Rho kinase inhibitor for cultivating the primary HPAEpiC is capable of, after sub-culturing and/or continuous culturing, effectively expanding the primary HPAEpiC and maintaining the alveolar epithelium characteristics of the primary HPAEpiC, and is also capable of preventing the primary HPAEpiC from differentiating into fibroblasts.

Therefore, the present disclosure provides a method for cultivating primary human pulmonary alveolar epithelial cells, which includes:

cultivating the primary human pulmonary alveolar epithelial cells in a first medium that includes a basal medium, a culture supplement, and a Rho kinase inhibitor, so as to obtain cultured primary human pulmonary alveolar epithelial cells; and cultivating the cultured primary human pulmonary alveolar epithelial cells in a second medium that includes the basal medium and the culture supplement, so as to obtain proliferated primary human pulmonary alveolar epithelial cells.

The culture supplement includes Jagged-1 (JAG-1) peptide, human Noggin protein (hNoggin) such as recombinant hNoggin, transforming growth factor-β (TGF-β) type I receptor inhibitor SB431542, human fibroblast growth factor 7 (hFGF-7) such as recombinant hFGF-7, human fibroblast growth factor 10 (hFGF-10) such as recombinant hFGF-10, and glycogen synthase kinase 3 (GSK-3) inhibitor CHIR99021.

As used herein, the term "culturing" can be used interchangeably with other terms such as "cultivation", and refers to sustaining, propagating and/or growing cells outside of organ systems or human body (e.g., in a sterile cell culture dish or flask). In addition, the term "cultivation" as used herein refers to use of a culture medium as a source of nutrients, hormones, and/or other factors which facilitates proliferation and/or maintenance of cells.

As used herein, the term "primary cells" refers to cells that are directly isolated from living tissues or organs (e.g., a biopsy material) and established for in vitro growth.

As used herein, the term "pulmonary alveolar epithelial cells" can be used interchangeably with other terms such as "alveolar epithelial cells (AECs)", "pulmonary epithelial cells" and "pneumocytes", and refers to epithelial cells positioned on the basement membrane of alveoli, including alveolar type 1 epithelial cells and alveolar type 2 epithelial cells.

According to the present disclosure, the primary HPAEpiC may be purchased commercially or isolated from living human tissues using standard techniques well known to those skilled in the art.

As used herein, the term "basal medium" refers to any basic medium which is usually a solution containing salts, nutrients, amino acids and vitamins for supporting or maintaining the growth of cells.

According to the present disclosure, those skilled in the art, based on their professional expertise and the physiological condition of the primary HPAEpiC, may choose a basic medium suitable for culturing such cells. Examples of the basal medium may include, but are not limited to, Dulbecco's Modified Eagle's Medium (DMEM), KnockOut™-DMEM, Minimum Essential Medium (MEM), α-MEM, Basal Medium Eagle (BME), Glasgow's Minimal Essential Medium, Advanced DMEM, DMEM/F-12 (Nutrient Mixture F-12), Ham's F-10 (Nutrient Mixture F-10), Iscove's Modified Dulbecco's Medium (IMDM), RPMI 1640 medium, and combinations thereof.

According to the present disclosure, the basal medium may be a commercially available epithelial cell medium which is optimized for promoting epithelial cell growth. Examples of the epithelial cell medium may include, but are not limited to, Epi Cell Basal Medium (Manufacturer: Cell Applications, Inc.), Bronchial/Tracheal Epithelial Cell Growth Medium (Manufacturer: Cell Applications, Inc.), Small Airway Epithelial Cell Growth Medium (Manufacturer: Lonza Group AG), Alveolar Epithelial Cell Medium (AEpiCM) (Manufacturer: ScienCell Research Laboratories, Inc.), and combinations thereof. In an exemplary embodiment, the basal medium is AEpiCM.

As used herein, the term "proliferate" or "proliferation" refers to an increase in the number of cells in a cell culture.

In an exemplary embodiment, the Rho kinase inhibitor is Y-27632.

According to the present disclosure, the Rho kinase inhibitor is present in a concentration ranging from 1 μM to 100 μM based on a total volume of the first medium. In certain embodiments, the Rho kinase inhibitor is present in a concentration ranging from 1 μM to 50 μM based on the total volume of the first medium. In an exemplary embodiment, the Rho kinase inhibitor is present in a concentration of 10 μM based on the total volume of the first medium.

According to the present disclosure, the JAG-1 peptide is present in a concentration ranging from 1 μM to 50 μM based on the total volume of the first medium. In certain embodiments, the JAG-1 peptide is present in a concentration ranging from 1 μM to 20 μM based on the total volume of the first medium. In an exemplary embodiment, the JAG-1 peptide is present in a concentration of 1 μM based on the total volume of the first medium.

According to the present disclosure, the hNoggin protein is present in a concentration ranging from 25 ng/mL to 200 ng/mL based on the total volume of the first medium. In certain embodiments, the hNoggin protein is present in a concentration ranging from 50 ng/mL to 150 ng/mL based on the total volume of the first medium. In an exemplary embodiment, the hNoggin protein is present in a concentration of 100 ng/mL based on the total volume of the first medium.

According to the present disclosure, the SB431542 is present in a concentration ranging from 2 μM to 20 μM based on the total volume of the first medium. In certain embodiments, the SB431542 is present in a concentration ranging from 3 μM to 15 μM based on the total volume of the first medium. In an exemplary embodiment, the SB431542 is present in a concentration of 10 μM based on the total volume of the first medium.

According to the present disclosure, the hFGF7 is present in a concentration ranging from 10 ng/mL to 200 ng/mL based on the total volume of the first medium. In certain embodiments, the hFGF7 is present in a concentration ranging from 50 ng/mL to 150 ng/mL based on the total volume of the first medium. In an exemplary embodiment, the hFGF7 is present in a concentration of 100 ng/mL based on the total volume of the first medium.

According to the present disclosure, the hFGF10 is present in a concentration ranging from 10 ng/mL to 200 ng/mL based on the total volume of the first medium. In certain embodiments, the hFGF10 is present in a concentration ranging from 50 ng/mL to 150 ng/mL based on the total volume of the first medium. In an exemplary embodiment, the hFGF10 is present in a concentration of 100 ng/mL based on the total volume of the first medium.

According to the present disclosure, the CHIR99021 is present in a concentration ranging from 1 μM to 10 μM based on the total volume of the first medium. In certain embodiments, the CHIR99021 is present in a concentration ranging from 1 μM to 5 μM based on the total volume of the first medium. In an exemplary embodiment, the CHIR99021 is present in a concentration of 3 μM based on the total volume of the first medium.

According to the present disclosure, the concentrations of JAG-1 peptide, hNoggin protein, SB431542, hFGF7, hFGF10, and CHIR99021 in the second medium (based on the total volume thereof) are similar to those in the first medium as described above.

According to the present disclosure, the primary human pulmonary alveolar epithelial cells may be cultivated in the first medium for a time period of at least 24 hours. In certain embodiments, the primary human pulmonary alveolar epithelial cells may be cultivated in the first medium for a time period ranging from 24 hours to 72 hours. In an exemplary embodiment, the primary human pulmonary alveolar epithelial cells are cultivated in the first medium for a time period of 24 hours.

According to the present disclosure, the primary human pulmonary alveolar epithelial cells may be cultivated in the second medium for a time period of at least 5 days. In certain embodiments, the primary human pulmonary alveolar epithelial cells may be cultivated in the second medium for a time period of at least 7 days. In an exemplary embodiment, the primary human pulmonary alveolar epithelial cells are cultivated in the second medium for a time period of at least 14 days.

According to the present disclosure, the primary human pulmonary alveolar epithelial cells may be cultivated in the first medium in the presence of a suitable culturing substrate. In certain embodiments, the primary human pulmonary alveolar epithelial cells may be cultivated in the first medium in the presence of an extracellular matrix (ECM).

As used herein, the term "extracellular matrix" refers to a substrate and/or scaffold that exists between somatic cells in animal tissues for providing structural support to tissues and an internal environment required for survival of somatic cells. The extracellular matrix is usually secreted by connective tissues, partially derived from cells with a basement membrane, and contains water, polysaccharides (including hyaluronan), elastin, glycoproteins (including collagen, entactin, fibronectin, and laminin), and other components.

According to the present disclosure, the ECM may be obtained by cultivation of ECM-producing cells (e.g., fibroblasts, chondrocytes, and a combination thereof), or may be commercially available biological agents. Examples of the ECM may include, but are not limited to, Extracellular Matrix Proteins [e.g., Type I collagen (Invitrogen), Type IV collagen (Sigma-Aldrich), gelatin (Sigma-Aldrich), and fibronectin (Corning)], basement membrane preparations [e.g., MATRIGEL® matrix (BD Biosciences), MATRIGEL® growth factor reduced (GFR) basement membrane matrix (Corning), Basement Membrane Extract (Sigma-Aldrich)], and synthetic material [e.g., ProNectin (Sigma-Aldrich)].

In certain embodiments, the ECM may be selected from the group consisting of MATRIGEL® GFR basement membrane matrix, MATRIGEL® matrix, and a combination thereof. In an exemplary embodiment, the ECM is MATRIGEL® GFR basement membrane matrix.

In certain embodiments, the ECM is first pre-coated on a bottom surface of a Petri dish, culture plate or flask used for cultivating primary human pulmonary alveolar epithelial cells, and then the primary human pulmonary alveolar epithelial cells suspended in the first medium are cultivated in the ECM-coated Petri dish, culture plate or flask.

The present disclosure also provides a kit for cultivating primary human pulmonary alveolar epithelial cells in vitro, which includes the basal medium, the culture supplement, and the Rho kinase inhibitor. In certain embodiments, each of the basal medium, the culture supplement, and the Rho kinase inhibitor is accommodated in a separate box or container. In certain embodiments, the kit may further include an ECM.

The applicant performed more extensive research and discovered that when primary human pulmonary alveolar epithelial cells were subjected to submerged cultivation in the first and second medium in sequence, and were then subjected to air-liquid interface cultivation in the second medium, the primary human pulmonary alveolar epithelial cells can effectively proliferate to form a three-dimensional cell culture of alveolar epithelium that was observed to possess characteristics and physiological functions similar to those of normal human alveolar epithelium.

Therefore, the present disclosure also provides a method for preparing a three-dimensional cell culture of alveolar epithelium, which includes:
  subjecting primary human pulmonary alveolar epithelial cells to submerged cultivation in a first medium that includes a basal medium, a culture supplement, and a Rho kinase inhibitor, so as to obtain cultured primary human pulmonary alveolar epithelial cells;
  subjecting the cultured primary human pulmonary alveolar epithelial cells to submerged cultivation in a second medium that includes the basal medium and the culture supplement, so as to obtain proliferated primary human pulmonary alveolar epithelial cells; and
  subjecting the proliferated primary human pulmonary alveolar epithelial cells to air-liquid interface cultivation in the second medium, so as to obtain the three-dimensional cell culture of alveolar epithelium.

The culture supplement includes JAG-1 peptide, hNoggin protein, SB431542, hFGF-7, hFGF-10, and CHIR99021.

As used herein, the term "three-dimensional cell culture" refers to growth of cells in an artificially-created environment in which the cells are permitted to proliferate [i.e., forming cell multilayers, clusters in suspension or growing on a scaffold (e.g., ECM)] and interact with its surroundings in all three dimensions.

As used herein, the term "air-liquid interface cultivation" refers to culturing of cells on a porous substrate, such that a top portion of the cells is in contact with the air and a bottom portion of the cells is in contact with the medium. For example, cells can be cultured in an open culture vessel having a filter insert containing a filter membrane, and a bottom side of the open culture vessel is added with a sufficient amount of a medium, so that the medium is permitted to contact the bottom portion of the cells positioned on the filter membrane without encapsulating or submerging the cells.

According to the disclosure, the porous substrate may be made of a material selected from the group consisting of polyethylene terephthalate, polyester, polycarbonate, and combinations thereof. The porous substrate may be uncoated or pre-coated with the ECM. In an exemplary embodiment, the porous substrate is an ECM-coated filter insert containing a filter membrane.

According to the present disclosure, the primary human pulmonary alveolar epithelial cells may be subjected to the submerged cultivation in the first medium for a time period of at least 24 hours. In certain embodiments, the primary human pulmonary alveolar epithelial cells may be subjected to the submerged cultivation in the first medium for a time period ranging from 24 hours to 72 hours. In an exemplary embodiment, the primary human pulmonary alveolar epithelial cells are subjected to the submerged cultivation in the first medium for a time period of 24 hours.

According to the present disclosure, the primary human pulmonary alveolar epithelial cells may be subjected to the submerged cultivation in the second medium for a time period of at least 10 days. In certain embodiments, the primary human pulmonary alveolar epithelial cells may be subjected to the submerged cultivation in the second medium for a time period ranging from 10 days to 24 days. In an exemplary embodiment, the primary human pulmonary alveolar epithelial cells are subjected to the submerged cultivation in the second medium for a time period of 17 days.

According to the present disclosure, the primary human pulmonary alveolar epithelial cells may be subjected to the air-liquid interface cultivation in the second medium for a time period of at least 7 days. In certain embodiments, the primary human pulmonary alveolar epithelial cells may be subjected to the air-liquid interface cultivation in the second medium for a time period ranging from 7 days to 14 days. In an exemplary embodiment, the primary human pulmonary alveolar epithelial cells are subjected to the air-liquid interface cultivation in the second medium for a time period of 14 days.

The three-dimensional cell culture of alveolar epithelium prepared according to the method of the present disclosure is capable of producing inflammatory response upon induction by viral proteins, and is capable of being infected by pseudovirus, and hence, is expected to be used as an in vitro model of alveolar epithelium.

Therefore, the present disclosure also provides a method for determining the effect of a test agent on alveolar tissues using an in vitro model of alveolar epithelium, which includes:

preparing the abovementioned three-dimensional cell culture of alveolar epithelium;

administering the test agent to the three-dimensional cell culture of alveolar epithelium; and analyzing the effect of the test agent on the three-dimensional cell culture of alveolar epithelium.

According to the present disclosure, the test agent may be selected from the group consisting of nanoparticles, environmental toxins or pollutants, tobacco smoke, cosmetic ingredients, chemical agents, drugs or pharmaceutical products, aerosol, radiation, naturally-occurring substances or biological materials (e.g., pollen, nucleic acids, peptides, viruses, bacteria, fungi, unicellular organisms, animal cells, etc.), and combinations thereof. In certain embodiments, the test agent may be a delivery vehicle of a therapeutic agent.

According to the present disclosure, the aforesaid method for determining the effect of the test agent on alveolar tissues may further include a step of subjecting the three-dimensional cell culture of alveolar epithelium to induction with a disease/disorder/symptom prior to the administration of the test agent.

Examples of the disease/disorder/symptom may include, but are not limited to, infection (e.g., viral infection, bacterial infection, fungal infection, etc.), toxicity effects, allergic reactions, adverse or side effects of drugs, cancer, metastasis of cancer cells, and combinations thereof.

The present disclosure will be further described by way of the following examples. However, it should be understood that the following examples are intended solely for the purpose of illustration and should not be construed as limiting the present disclosure in practice.

EXAMPLES

General Experimental Materials:
1. Source and Preliminary Amplification of Primary Human Pulmonary Alveolar Epithelial Cells (HPAEpiC)

The primary HPAEpiC used in the following examples were purchased from ScienCell Research Laboratories, Inc., CA, USA (Catalogue No. 3200), and preliminary amplification thereof was performed according to the manufacturer's operating instruction. First, a microcentrifuge tube containing the frozen primary HPAEpiC was removed from a liquid nitrogen storage tank, and was then placed into a water bath having a temperature of 37° C. to be thawed. Next, the thus thawed primary HPAEpiC were seeded at a density ranging from $1.0 \times 10^4$ cells/cm$^2$ to $1.5 \times 10^4$ cells/cm$^2$ into a T-25 flask (the bottom side thereof being pre-coated with 2 µg/cm$^2$ poly-L-lysine) containing a basal medium supplemented with 1% Epithelial Cell Growth Supplement (EPiCGS) (Manufacturer: ScienCell Research Laboratories, Inc.; Catalogue No.: 4152), followed by cultivation overnight in an incubator with culture conditions set at 37° C. and 5% $CO_2$. The basal medium in the T-25 flask was replaced on the next day with a fresh basal medium, thereby obtaining cultured primary HPAEpiC.

2. Basal Medium

Unless specified otherwise, the primary HPAEpiC were cultured in alveolar epithelial cell medium (AEpiCM) (Manufacturer: ScienCell Research Laboratories, Inc.; Catalogue No.: 3201) that served as a basal medium and that was supplemented with 2% fetal bovine serum (FBS) (Manufacturer: ScienCell Research Laboratories, Inc.; Catalogue No.: 0010) and 1% penicillin-streptomycin (Manufacturer: ScienCell Research Laboratories, Inc.; Catalogue No.: 0503).

3. Supplementary Components

The various supplementary components used in the following experiments and sources thereof are shown in Table 1 below.

TABLE 1

| Supplementary component | Source (Manufacturer) |
| --- | --- |
| Jagged-1 (JAG-1) peptide | AnaSpec, Cat. No.: AS-61298 |
| Recombinant human Noggin protein (hNoggin) | R&D Systems, Cat. No.: 6057-NG |
| SB431542 [transforming growth factor-β (TGF-β) type I receptor inhibitor] | Sigma-Aldrich, Cat. No.: S4317 |
| Recombinant human fibroblast growth factor 7 (hFGF7) | R&D Systems, Cat. No.: 251-KG |
| Recombinant human fibroblast growth factor 10 (hFGF10) | R&D Systems, Cat. No.: 345-FG |
| CHIR99021 [glycogen synthase kinase 3 (GSK-3) inhibitor] | Sigma-Aldrich, Cat. No.: SML1046 |
| Y-27632 [Rho kinase inhibitor (Rock inhibitor)] | Sigma-Aldrich, Cat. No.: SMC075 |

General Experimental Procedures:
1. Immunofluorescence Staining Assay

After removal of the basal medium, the monolayer of primary HPAEpiC was washed twice with Dulbecco's Phosphate Buffered Saline (DPBS), and then a Cytofix/Cytoperm™ fixation and permeabilization solution (Manufacturer: BD Biosciences; Catalogue No.: 554722) was added at room temperature to fix and permeabilize the cells for 15 minutes. Next, the solution was removed and the cells were washed twice with DPBS, followed by adding DPBS supplemented with 5% FBS and incubating the cells at room temperature for 30 minutes to 60 minutes to block non-specific binding. After that, the cells were subjected to incubation with an appropriate amount of a primary antibody at room temperature for 90 minutes to 120 minutes, followed by washing twice with DPBS. If the primary antibody did not carry a fluorescent label, the cells were further incubated with a secondary antibody at room temperature for 90 minutes to 120 minutes.

Then, the cells were washed twice with DPBS and then air-dried at room temperature for 5 minutes. Afterwards, the cells were mounted using VECTASHIELD® Antifade Mounting Medium with DAPI (Manufacturer: Vector Laboratories; Catalogue No.: H-1200), and were then observed and photographed under a confocal laser scanning microscope (Manufacturer: Leica Microsystems; Model No.: SP8). The ratio of fluorescent cells was determined using ImageXpress Micro 4 High-Content Imaging System with MetaXpress® High-Content Image Acquisition and Analysis software (version 6.5) (Manufacturer: Molecular Devices, LLC).

The primary antibody and/or the secondary antibody used in the immunofluorescence staining assay for detecting the respective protein in the cultured HPAEpiC are shown in Table 2 below.

TABLE 2

| Proteins | Primary antibody (Manufacturer; Catalogue No.; dilution factor) | Secondary antibody (Manufacturer; Catalogue No.; dilution factor) |
|---|---|---|
| Lung alveolar type 1 cell-specific apical membrane protein-56 (HT1-56) | Mouse anti-HT1-56 IgG1 antibody (Terrace Biotech; TB-29 AHT1-56; 1:50) | Alexa-Fluor® 555-conjugated goat-anti-mouse IgG1 antibody (Thermo Fisher Scientific; A-21127;1:200) |
| Lung alveolar type 2 cell-specific apical membrane protein-56 (HT2-280) | Mouse anti-HT2-280 IgM antibody (Terrace Biotech; TB-27 AHT2-280; 1:50) | Alexa-Fluor® 488-conjugated goat-anti-mouse IgM antibody (Thermo Fisher Scientific; A-21042; 1:200) Alexa-Fluor® 633-conjugated goat-anti-mouse IgM antibody (Thermo Fisher Scientific; A-21046; 1:200) |
| Epithelial cell adhesion molecule (EpCAM) | PerCP/Cy5.5®-conjugated mouse anti-EpCAM antibody (BioLegend; 324214; 1:100) Alexa-Fluor® 647-conjugated mouse-anti-EpCAM antibody (Cell Signaling; 5447; 1:400) | — |
| Vimentin | Alexa-Fluor® 488-conjugated rabbit anti-Vimentin antibody (Cell Signaling; 9854S; 1:400) | — |
| Zonula occludens-1 (ZO-1) | Alexa-Fluor® 488-conjugated mouse anti-ZO-1 antibody (Thermo Fisher Scientific; 339188; 1:100) | — |
| Surfactant protein B (SPB) | Mouse anti-SPB IgG2 antibody (Thermo Fisher Scientific; MA1-204; 1:100) | Alexa-Fluor® 488-conjugated goat-anti-mouse IgG antibody (Jackson ImmunoResearch Laboratories; 115-545-062; 1:200) |
| Pro-surfactant protein C (pro-SPC) | Rabbit anti-pro-SPC IgG2 antibody (Sigma-Aldrich; AB3786; 1:200) | Cy3-conjugated goat anti-rabbit IgG antibody (Sigma-Aldrich; AP132C; 1:200) |
| Angiotensin-converting enzyme 2 (ACE2) | Rabbit anti-ACE2 IgG antibody (abcam; ab87436; 1:100) | Alexa-Fluor® 488-conjugated goat-anti-rabbit IgG antibody (Jackson ImmunoResearch Laboratories; 115-545-144; 1:200) |
| Transmembrane protease serine 2 (TMPRSS2) | Mouse anti-TMPRSS2 IgG1 antibody (Santa Cruz Biotechnology; sc-515727; 1:100) | Alexa-Fluor® 633-conjugated goat-anti-mouse IgM antibody (Thermo Fisher Scientific; A-21046; 1:200) |

2. Statistical Analysis

All the experiments described below were performed in triplicates. The experimental data of all the test groups are expressed as mean±standard error of the mean (SEM), and were analyzed using two-way analysis of variance (ANOVA) or two-tailed Student's t-test with GraphPad Prism software version 8.0.2 (Developer: GraphPad Software, Inc., San Diego, CA), so as to assess differences between the groups. Statistical significance is indicated by $p<0.05$.

Example 1. Evaluation of the Effect of Different Supplementary Components on Cultivation of Primary HPAEpiC In order to evaluate the effect of different types of supplementary components on the morphology of primary HPAEpiC, the applicant added various supplementary components to the basal medium and then separately performed sub-culturing and continuous culturing of the primary HPAEpiC for a long period of time. In addition, a commercially available culture medium, i.e., EPiCGS described in section 1 of the General Experimental Materials, served as a control group.

A. Sub-Culturing of Primary HPAEpiC

Experimental Procedures:

The cultured primary HPAEpiC obtained in section 1 of the General Experimental Materials were seeded at a concentration of $1\times10^5$ cells per well into respective wells of 6-well plates. Each well had a bottom side pre-coated with 8.7 µg/cm$^2$ of MATRIGEL® Growth Factor Reduced (GFR) Basement Membrane Matrix (Manufacturer: Corning; Catalogue No.: 354230; Lot. No.: 9133005). The seeded primary HPAEpiC were divided into 4 experimental groups, namely, experimental group B (abbreviated as EGB), experimental group BM (abbreviated as EGBM), experimental group G (abbreviated as EGG), and experimental group GM (abbreviated as EGGM), followed by culturing the primary HPAEpiC in a first medium (i.e., using basal medium for EGB, using basal medium and various supplementary components including Y-27632 for EGBM, using basal medium, EpiCGS and the various supplementary components including Y-27632 for EGGM, and using basal medium and EpiCGS for EGG, as shown in Table 3 below), so as to obtain a first generation of primary HPAEpiC (hereinafter referred to as "P1 cells").

TABLE 3

| Supplementary component (concentration) | EGB | EGBM | EGG | EGGM |
|---|---|---|---|---|
| EpiCGS (1%) | − | − | + | + |
| JAG-1 (1 µM) | − | + | − | + |
| hNoggin (100 ng/mL) | − | + | − | + |
| SB431542 (10 µM) | − | + | − | + |
| hFGF7 (100 ng/mL) | − | + | − | + |
| hFGF10 (100 ng/mL) | − | + | − | + |
| CHIR99021 (3 µM) | − | + | − | + |
| Y-27632* (10 µM) | − | + | − | + |

*only added into the basal medium on the first day after start of cultivation, and omitted during subsequent sub-culturing The P1 cells in each experimental group were cultivated in an incubator with culture conditions set at 37° C. and 5% $CO_2$, and medium change was performed every 2 to 3 days. Sub-culturing in a second medium (i.e., using the basal medium for EGB, using the basal medium and the various supplementary components excluding Y-27632 for EGBM, using the basal medium, EpiCGS and the various supplementary components excluding Y-27632 for EGGM, and using the basal medium and EpiCGS for EGG) was performed when the cultured P1 cells reached 90% of confluence, thereby obtaining a second generation of primary HPAEpiC (hereinafter referred to as "P2 cells"). Thereafter, the cultured P2 cells were subjected to sub-culturing in the second medium when reaching 90% of confluence, thereby obtaining a third generation of primary HPAEpiC (hereinafter referred to as "P3 cells"). An optical microscope (Manufacturer: Nikon Corporation; Model No.: Eclipse TS100 & Eclipse Ti) was used for imaging and capturing photographs of the P1 cells on the second day after starting cultivation and each of the P2 cells and P3 cells on the sixth day after starting cultivation at a magnification of 100×.

In addition, on the eighth day after starting cultivation of each of the P1 cells and P2 cells, a portion of the P1 cells and a portion of the P2 cells in the EGBM and EGGM were subjected to immunofluorescence staining using the procedures described in section 1 of the General Experimental Procedures and the antibodies shown in Table 2 for detection of lung alveolar type 1 cell-specific apical membrane protein-56 (HT1-56) and lung alveolar type 2 cell-specific apical membrane protein-280 (HT2-280) as markers of alveolar type 1 epithelial cells (AT1 cells) and alveolar type 2 epithelial cells (AT2 cells), respectively.

Results:

FIG. 1 shows the cell morphology of the P1 cells, P2 cells and P3 cells in each of EGB, EGBM, EGG, and EGGM as observed using optical microscopy. As shown in FIG. 1, on the second day after starting cultivation, most of the P1 cells in the EGB were round-shaped and existed in a suspended condition, indicating that the cells cannot attach to the bottom of the well for proper growth. On the fifth day after starting cultivation, sub-culturing of the P1 cells in the EGB was no longer possible because the number of surviving P1 cells was very low (not shown). In contrast, the P1 cells in the EGBM, EGG and EGGM can be successfully sub-cultured into P3 cells with good attachment to the bottom of the well. However, most of the P2 cells and P3 cells in the EGG had changed their morphology by becoming slender, spindle-shaped, and it is presumed that these cells had differentiated into fibroblasts. It is noted that only the P3 cells in the EGBM and EGGM still maintained their cobblestone-shaped morphology, and that the number of P3 cells in the EGGM was greater compared to that of EGBM.

Figure 2:
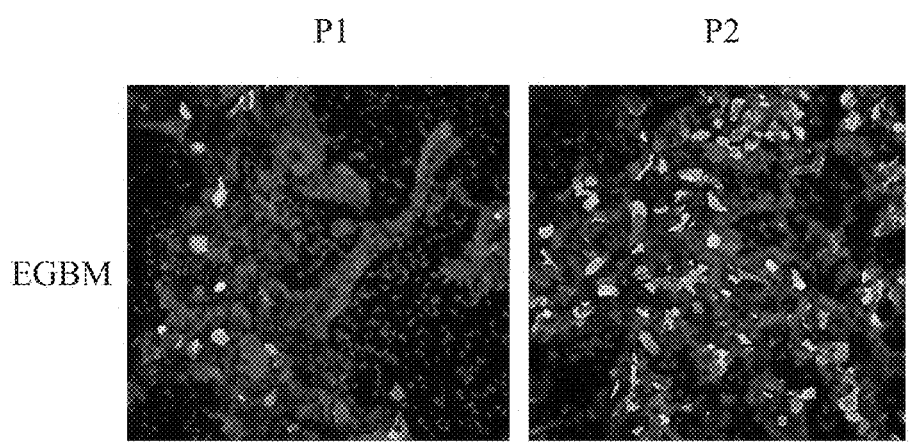
FIG. 2 shows the result of immunofluorescence staining assay performed on the P1 cells and P2 cells in the EGBM of Example 1, infra, in which the alveolar type 1 epithelial cells (AT1 cells), the alveolar type 2 epithelial cells (AT2 cells) and cell nuclei were respectively represented by red, green, and blue fluorescence.

FIG. 2 shows the result of the immunofluorescence staining assay of the P1 cells and P2 cells in the EGBM group. As shown in FIG. 2, both the AT1 cells and AT2 cells respectively represented by the green and red fluorescence could be detected among the P1 cells and P2 cells in the EGBM. The P1 cells and the P2 cells in the EGGM also demonstrated similar pattern of immunofluorescence staining (data not shown).

These results suggest that addition of Rock inhibitor (i.e., Y-27632) and a culture supplement including JAG-1 peptide, hNoggin protein, SB431542, hFGF7, and hFGF10, and CHIR99021 to the basal medium for starting the cultivation of the primary HPAEpiC (see the EGBM and EGGM in Table 3), followed by sub-culturing using the culture supplement excluding the Y-27632 added to the basal medium, not only contributed to the survival, amplification and sub-culturing of the primary HPAEpiC, but also effectively maintained the normal morphology and physiological functions of the primary HPAEpiC (especially the proliferation and differentiation of the AT1 and AT2 cells). In comparison, the commercially available culture supplement, i.e., EpiCGS, was only useful in the attachment and survival of the primary HPAEpiC during the initial stage of the culture, and not only failed to improve sub-culturing of the primary HPAEpiC, but also might cause the primary HPAEpiC to lose their normal morphology or differentiate into undesired types of cells.

B. Continuous Culturing of Primary HPAEpiC

Experimental Procedures:

The P1 cells in the EGG and EGGM described in the abovementioned section entitled "A. Sub-culturing of primary HPAEpiC" were placed in an incubator with culture condition set at 37° C. and 5% $CO_2$, and medium change was performed every 2 to 3 days by adding the various supplementary components including Y-27632 as shown in Table 3. On the first day and fifth day after starting cultivation, a portion of the P1 cells in the EGG and EGGM were subjected to immunofluorescence staining using the procedures described in section 1 of the General Experimental Procedures and the antibodies shown in Table 2 for detection of epithelial cell adhesion molecule (EpCAM) and vimentin proteins as markers of epithelial cells and fibroblasts, respectively, followed by quantification of the percentage ratio of EpCAM P1 cells and Vimentin$^+$ P1 cells. The difference between the thus obtained percentage ratio of EpCAM P1 cells and Vimentin$^+$ P1 cells in the EGG and that in the EGGM were analyzed using two-way ANOVA according to the procedures described in section 2 of the General Experimental Procedures.

Figure 3:
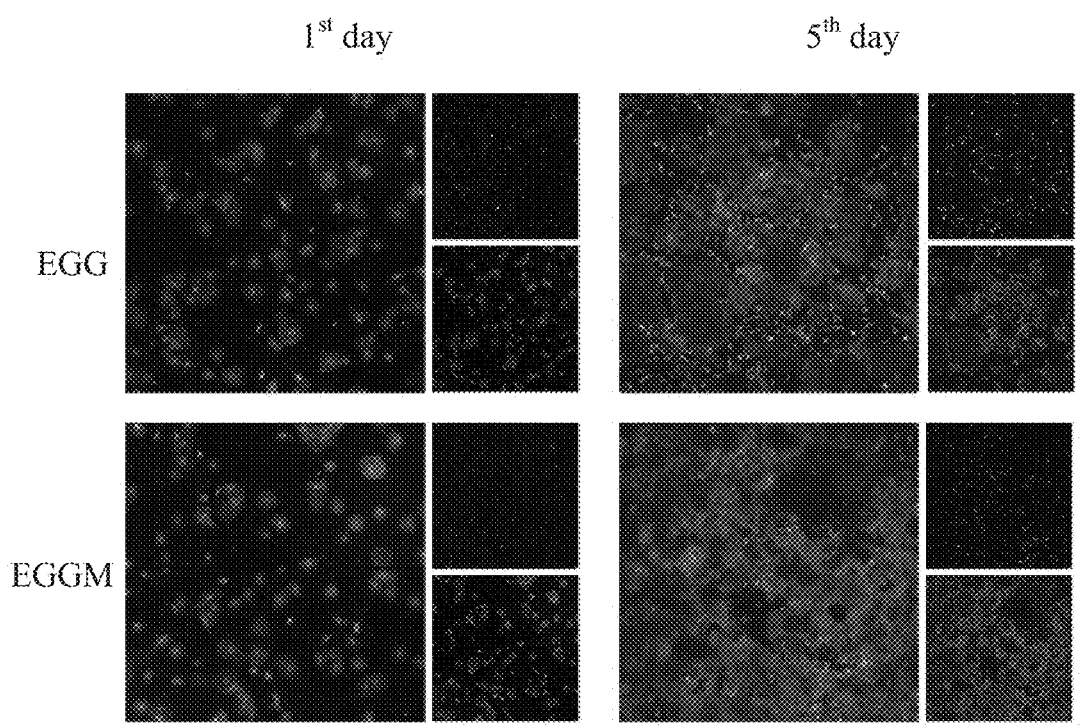
FIG. 3 shows the result of immunofluorescence staining assay performed on the P1 cells in the EGG and EGGM of Example 1, infra, in which EpCAM$^+$ P1 cells, Vimentin$^+$ P1 cells and cell nuclei were respectively represented by red, green, and blue fluorescence.

Results:

FIG. 3 shows the result of immunofluorescence staining assay of P1 cells in the EGG and EGGM on the first and fifth days after starting cultivation. As shown in FIG. 3, the expression level of EpCAM proteins in the P1 cells, which was represented by red fluorescence, decreased in the EGG with increased number of days of cultivation, as compared with a high level of expression in the EGGM which was maintained throughout the culturing period from the first day to the fifth day. In addition, the expression level of the intermediate filament protein, i.e., vimentin, in the P1 cells, which was represented by the green fluorescence, greatly increased in the EGG with increased number of days of cultivation, as compared with that in the EGGM which only showed a slight increase up to the fifth day after starting cultivation.

Figure 4:
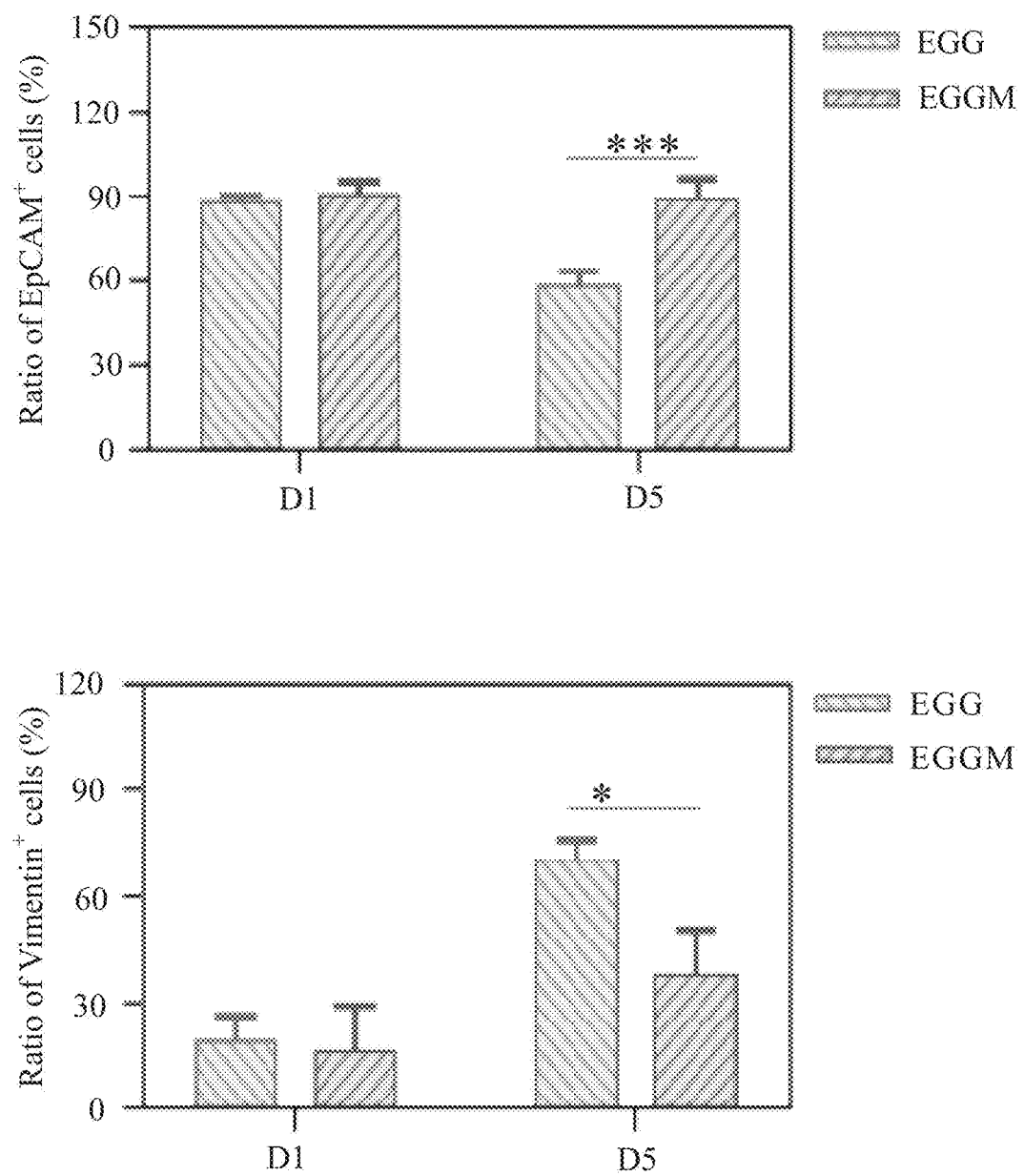
FIG. 4 are graphs respectively showing the percentage ratios of EpCAM$^+$ P1 cells and Vimentin$^+$ P1 cells in the EGG and EGGM which were determined based on the immunofluorescence staining assay result shown in FIG. 3, in which the symbol "*" represents $p<0.05$ compared with the EGGM, and the symbol "***" represents $p<0.001$ compared with the EGG.

FIG. 4 shows the percentage ratios of EpCAM$^+$ P1 cells and Vimentin$^+$ P1 cells in the EGG and EGGM on the first and fifth days after starting cultivation which were determined based on the result of immunofluorescence staining assay. As shown in the upper panel of FIG. 4, the percentage ratio of EpCAM$^+$ P1 cells in the EGG significantly decreased with increased number of days of cultivation, while that in the EGGM was maintained at a high level throughout the culturing period from the first day to the fifth day. On the other hand, the lower panel of FIG. 4 shows the percentage ratio of vimentin$^+$ P1 cells in the EGG significantly increased with increased number of days of cultivation, as compared to that in the EGGM which only showed a slight increase up to the fifth day after starting cultivation and was still significantly lower than that of the EGG.

These results suggest that under the condition of not subjecting the primary HPAEpiC to sub-culturing, addition of Y-27632 and the culture supplement including a combination of JAG-1, hNoggin, SB431542, hFGF7, hFGF10, and CHIR99021 into the basal medium during the continuous culturing period can effectively maintain the epithelium characteristics of the primary HPAEpiC and avoid differentiation of the same into fibroblasts.

Based on the aforesaid results, the applicant decided to utilize the aforesaid basal medium and the culture supplement containing the various supplementary components shown in Table 3 but excluding the Y-27632 (hereinafter referred to as "GM medium") in the following experiments.

Example 2. Preparation of Three-Dimensional (3D) Cell Culture of Alveolar Epithelium and Characterization of the Same In the following experiments, the applicant employed the primary HPAEpiC that had been subjected to sub-culturing and the GM medium as mentioned in Example 1 to prepare a 3D cell culture of alveolar epithelium, and then performed characterization of the thus obtained 3D cell culture of alveolar epithelium.

A. Preparation of 3D Cell Culture of Primary HPAEpiC

The primary HPAEpiC that had been subjected to sub-culturing using the GM medium (i.e., the basal medium containing the various supplementary components but excluding the Y-27632) as described in Example 1 were seeded at a concentration of $1.5 \times 10^5$ cells per well into respective permeable transwell inserts for a 24-well plate. Each of the transwell inserts had a bottom side pre-coated with 8.7 μg/cm$^2$ MATRIGEL® GFR basement membrane matrix (Manufacturer: Falcon; Catalogue No.: 353095) and contained 0.3 mL of GM medium. The transwell inserts were placed into the 24-well plate that contained 0.7 mL of GM medium in each well, followed by subjecting the primary HPAEpiC to submerged cultivation in an incubator with culture conditions set at 37° C. and 5% $CO_2$. Medium change (i.e., with fresh GM medium) was performed on the second day of the submerged cultivation and then every 2 to 3 days, so that the primary HPAEpiC formed a cell monolayer in the transwell inserts.

On the eighteenth day after starting submerged cultivation, the GM medium was removed from the transwell inserts, and the primary HPAEpiC were subjected to air-liquid interface cultivation for 14 days in an incubator with culture conditions set at 37° C. and 5% $CO_2$. Medium change was performed every 2 to 3 days by adding fresh GM medium into the 24-well plates without adding the same into the transwell inserts. On the seventh day after starting the air-liquid interface cultivation, the cultured HPAEpiC cells were observed to be accumulated and were arranged tightly with an obvious connection pattern therebetween and thereamong, indicating formation of a 3D cell culture of alveolar epithelium.

B. Immunofluorescence Staining Assay

Experimental Procedures:

On the eighteenth day after starting the submerged cultivation, and on the eighth and the fifteenth days after starting the air-liquid interface cultivation, the cultured primary HPAEpiC were harvested and subjected to immunofluorescence staining using the procedures described in section 1 of the General Experimental Procedures and the antibodies shown in Table 2 for detection of HTI-56 and HT2-280 proteins as markers of AT1 cells and AT2 cells, respectively, as well as detection of surfactant protein B (SPB) and pro-surfactant protein C (pro-SPC) as markers of AT2 cells. In addition, on the fifteenth day after starting the air-liquid interface cultivation, the cultured primary HPAEpiC were also harvested separately and subjected to immunofluorescence staining and the antibodies shown in Table 2 for detection of HT2-280 and zonula occludens-1 (ZO-1) proteins as markers of AT2 cells and tight junctions, respectively.

Figure 5:
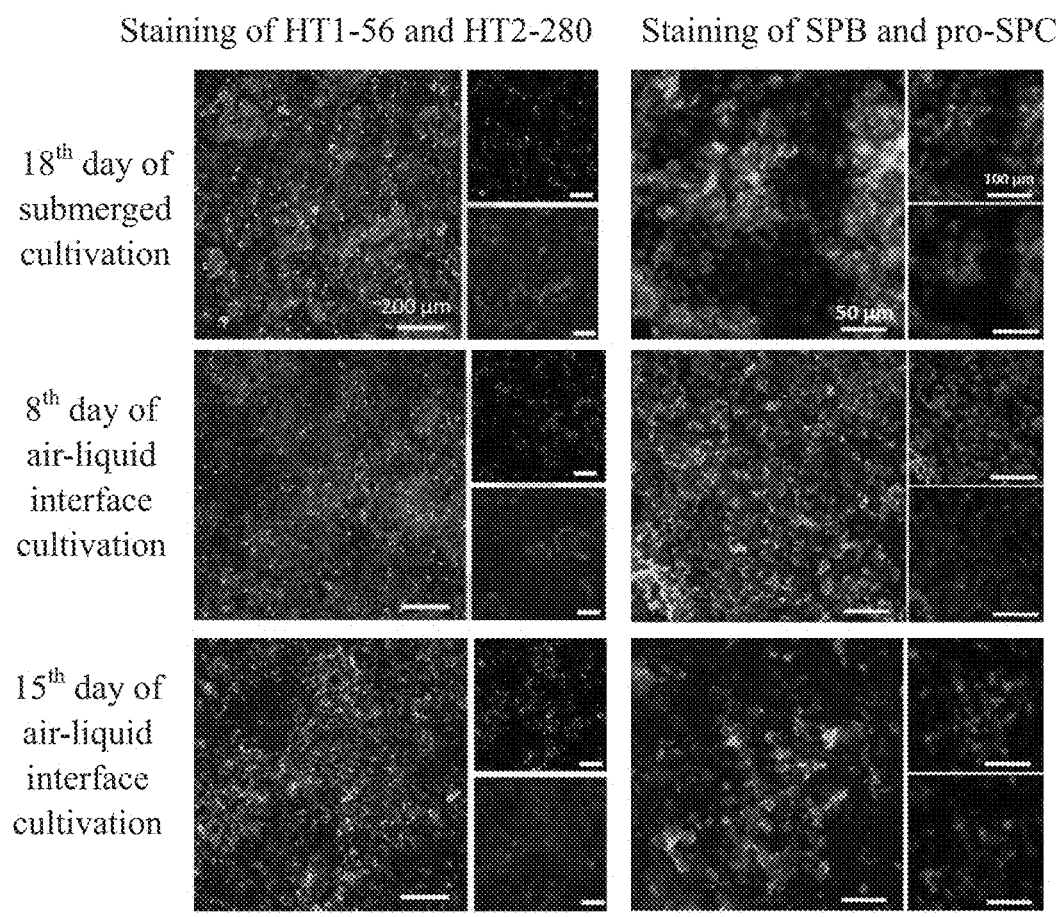
FIG. 5 shows the result of immunofluorescence staining assay for detection of HT1-56 and HT2-280 proteins (i.e., markers of AT1 cells and AT2 cells, respectively), as well as SPB and pro-SPC proteins (i.e., markers of the AT2 cells), in the cultured primary HPAEpiC of Example 2, infra, in which HT1-56 and HT2-280 proteins were respectively represented by red and green fluorescence, while SPB protein, pro-SPC proteins and cell nuclei were represented by green, red and blue fluorescence, respectively.

Results:

FIG. 5 shows the result of the immunofluorescence staining assay of the cultured primary HPAEpiC harvested on the eighteenth day after starting the submerged cultivation and those obtained on the eighth and fifteenth days after starting the air-liquid interface cultivation (such cells were stained for detection of HT1-56 and HT2-280 proteins as markers of AT1 cells and AT2 cells respectively, as well as SPB and pro-SPC proteins as markers of the AT2 cells). As shown in FIG. 5, the AT1 cells and AT2 cells respectively represented by the red and green fluorescence were detected in the cultured primary HPAEpiC harvested on the eighteenth day after starting the submerged cultivation and those obtained on the eighth and fifteenth days after starting the air-liquid interface cultivation (see the left panel), and the thus detected AT2 cells were capable of expressing the SPB and pro-SPC proteins as represented by the green and red fluorescence, respectively (see the right panel).

Figure 6:
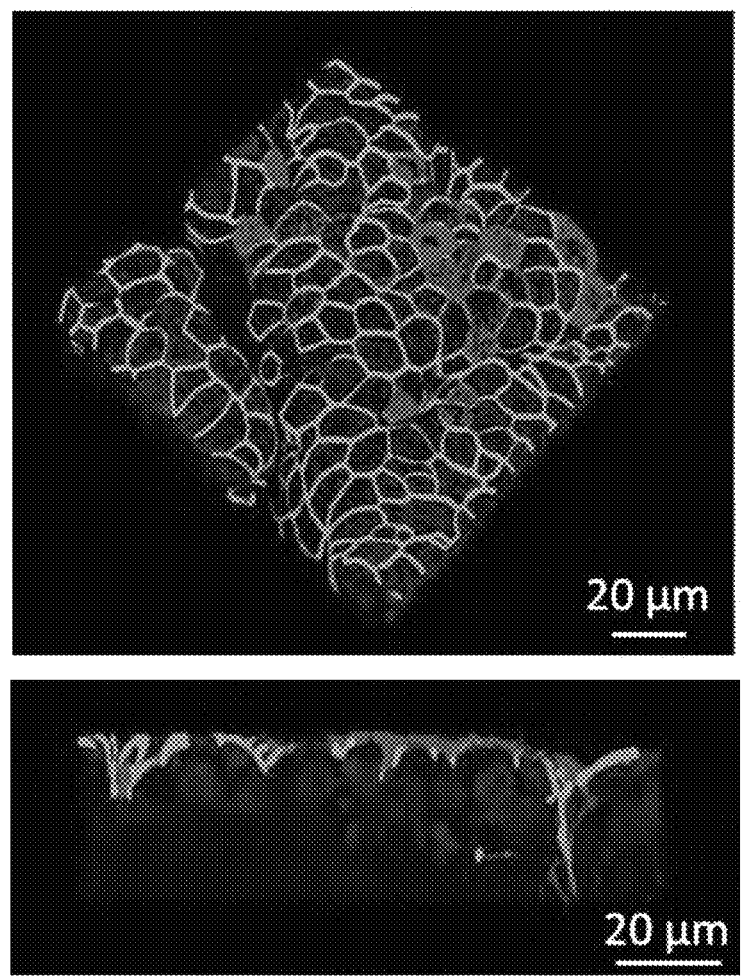
FIG. 6 shows the result of immunofluorescence staining assay for detection of HT2-280 and ZO-1 proteins (i.e., markers of AT2 cells and tight junctions, respectively) in the cultured primary HPAEpiC of Example 2, infra, in which the ZO-1 protein, the HT2-280 protein and the cell nuclei were respectively represented by green, red and blue fluorescence.

FIG. 6 shows the result of the immunofluorescence staining assay of the cultured primary HPAEpiC harvested on the fifteenth day after starting the air-liquid interface cultivation (such cells were stained for detection of HT2-280 and ZO-1 proteins as markers of AT2 cells and tight junctions, respectively). As shown in FIG. 6, the cultured primary HPAEpiC had formed tight junctions as evidenced by normal expression of ZO-1 protein (see the green fluorescence).

C. Scanning Electron Microscopy Analysis

Figure 7:
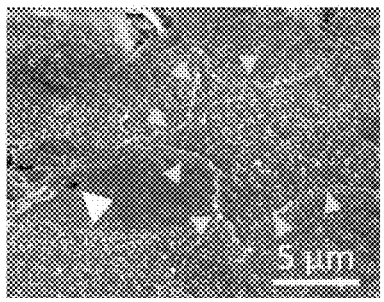
FIG. 7 shows scanning electron microscopy images of the 3D cell culture of alveolar epithelium of Example 2, infra, in which the yellow-colored and the white-colored arrow heads respectively indicate tight junctions and secretion pores.
Figure 7:
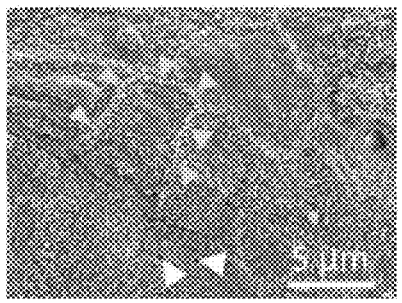
Figure 7:
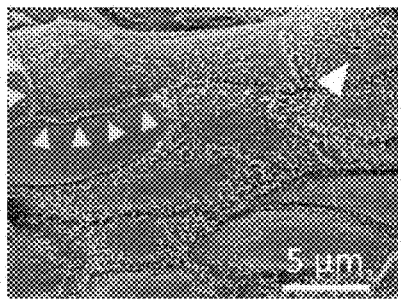
Figure 7:
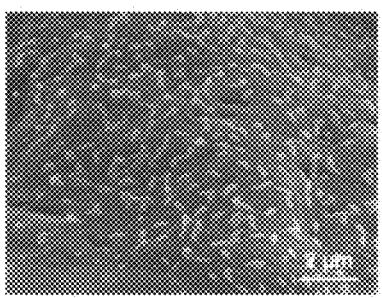
Figure 7:
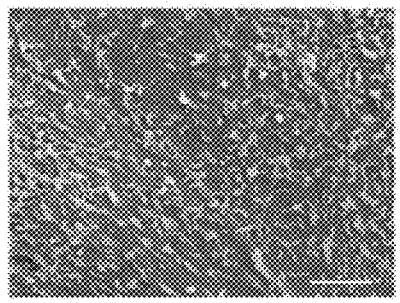
Figure 7:
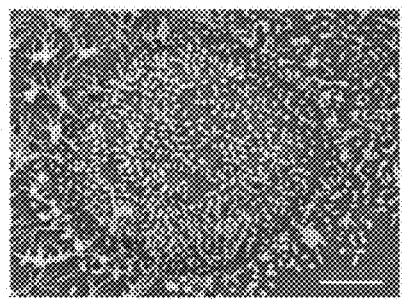

Experimental Procedures:

On the eighteenth day after starting the submerged cultivation, and on the eighth and the fifteenth days after starting the air-liquid interface cultivation, the cultured primary HPAEpiC were harvested and washed three times with DPBS, and then an appropriate amount of a 2.5% glutaraldehyde solution dissolved in DPBS was added to fix the cells for 1 hour. Next, the thus fixed cells were washed three times with DPBS, and were then subjected to dehydration treatment performed in sequence using ethanol solutions having concentrations of 35%, 50%, 75%, 85%, 95% and 99.8% (v/v), respectively. Thereafter, the cells were treated with hexamethyldisilazane (HDMS) for 5 minutes, and were then left overnight so as to form a cell film layer. Subsequently, the cell film layer was removed from the transwell insert, and was subjected to coating with platinum using techniques well-known to those skilled in the art, followed by imaging and photography under an ultra-high resolution thermal field emission scanning electron microscope (SEM) (Manufacturer: JEOL, Ltd.; Model No.: JSM-7610F) at magnifications of 2500× and 5000×.
Results:

FIG. 7 shows SEM images of the cultured primary HPAEpiC harvested on the eighteenth day after starting the submerged cultivation and on the eighth and fifteenth days after starting the air-liquid interface cultivation. As shown by the upper panel of FIG. 7, tight junctions (indicated by yellow-colored arrow heads) formed between the HPAEpiC harvested on the eighteenth day after starting the submerged cultivation were observed, and elliptical-shaped secretion pores (indicated by white arrow heads) were further observed on the surface of the AT2 cells of the cultured primary HPAEpiC. In addition, the cultured HPAEpiC harvested on the eighth and fifteenth days after starting the air-liquid interface cultivation showed an increased number of the secretion pores, as well as a more compact arrangement and 3D configuration, which was not readily observed in the cultured primary HPAEpiC harvested on the eighteenth day after starting the submerged cultivation.

As shown by the lower panel of FIG. 7, short protrusions formed on the surface of the primary HPAEpiC harvested on the eighteenth day after starting the submerged cultivation were observed. In comparison, the cultured primary HPAEpiC harvested on the eighth and fifteenth days after starting the air-liquid interface cultivation were observed to have increase in number and density of short protrusions as well as significantly increase in short protrusion length (increase to approximately 0.4 μm to 1.0 μm), indicating that the alveolar epithelium of the cultured primary HPAEpiC had a more developed structure of microvilli.

These results suggest that cultured primary HPAEpiC are capable of forming a three-dimensional configuration of alveolar epithelium after being subjected to air-liquid interface cultivation for at least 8 days, and that AT1 and AT2 cells of the 3D cell culture of alveolar epithelium prepared from the method of the present disclosure not only can maintain normal growth and physiological functions, but also can possess characteristics of normal human alveolar epithelium.

Figure 8:
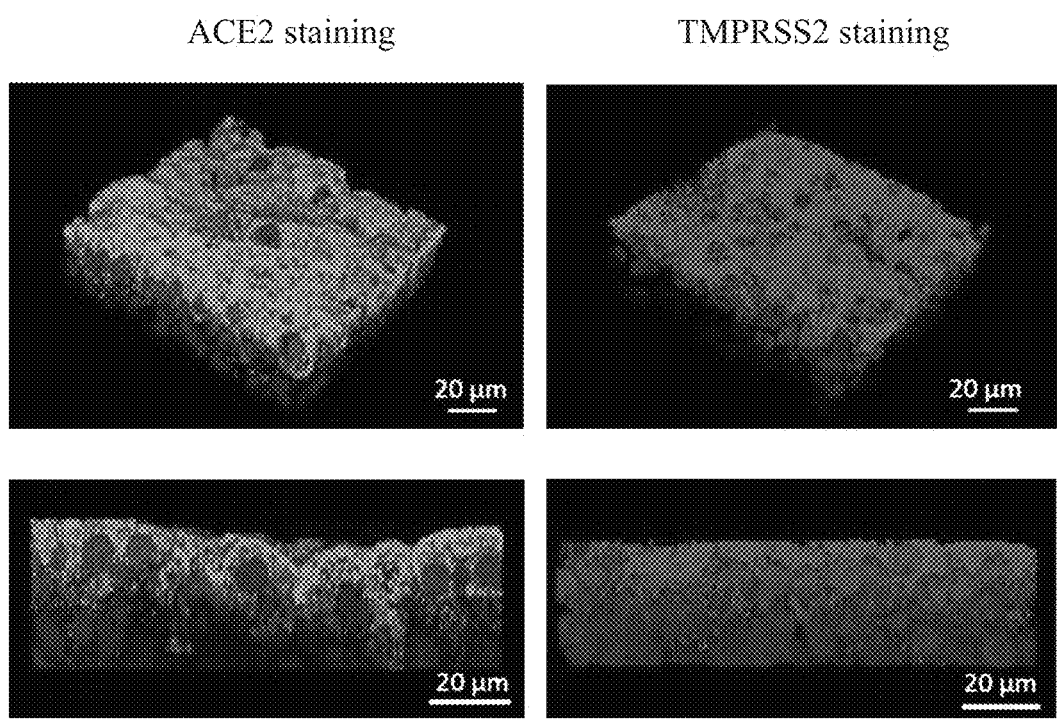
FIG. 8 shows the result of immunofluorescence staining assay for detection of ACE2 and TMPRSS2 proteins in the 3D cell culture of alveolar epithelium of Example 3, infra, in which the ACE2 protein, the TMPRSS2 protein and the cell nuclei were respectively represented by green, red and blue fluorescence.

Example 3. Evaluation of 3D Cell Culture of Alveolar Epithelium as an In Vitro Model of Alveolar Epithelium for Viral Infection In the following experiments, the applicant utilized severe acute respiratory syndrome coronavirus 2 (SARS-CoV-2) to infect the 3D cell culture of alveolar epithelium prepared and evaluated in Example 2, so as to determine its feasibility as an in vitro model of alveolar epithelium for viral infection.
Experimental Materials:
1. Source of SARS-CoV-2 Pseudovirus SARS-CoV-2 pseudovirus, which is a SARS-CoV-2 spike pseudotyped lentivirus having a viral envelope expressing SARS-CoV-2 spike protein fused to green fluorescence protein (GFP), was purchased from the RNA Technology Platform and Gene Manipulation Core, Institute of Molecular Biology, Academia Sinica, Taiwan (Catalogue No.: nCoV-S-GFP).
A. Detection of Host Cell Proteins Involved in SARS-CoV-2 Infection
Experimental Procedures:

The primary HPAEpiC that had been subjected to sub-culturing using the GM medium (i.e., the basal medium containing the various supplementary components but excluding the Y-27632) as described in Example 1 were subjected to submerged cultivation and air-liquid interface cultivation using the procedures described in section A of Example 2, and on the eighth day after starting the air-liquid interface cultivation, the thus formed 3D cell culture of alveolar epithelium was harvested and subjected to immunofluorescence staining assay using the procedures described in section 1 of the General Experimental Procedures for detection of angiotensin-converting enzyme 2 (ACE2) and transmembrane protease serine 2 (TMPRSS2) proteins, which are host cell proteins involved in the entry of SARS-CoV-2 into the host cell and initial priming of the SARS-CoV-2 spike protein in the host cell, respectively.
Results:

FIG. 8 shows the result of the immunofluorescence staining assay for detection of proteins associated with SARS-CoV-2 infection in the 3D cell culture of alveolar epithelium that was harvested on the eighth day after starting the air-liquid interface cultivation. As shown in FIG. 8, two proteins associated with SARS-CoV-2 infection, i.e., ACE2 and TMPRSS2 proteins respectively represented by the green and red fluorescence, were detected in the 3D cell culture of alveolar epithelium.
B. Verification of SARS-CoV-2 Pseudovirus Infection
Experimental Procedures:

The primary HPAEpiC that had been subjected to sub-culturing using the GM medium (i.e., the basal medium containing the various supplementary components but excluding the Y-27632) as described in Example 1 were divided into 4 test groups, i.e., experimental groups 1 to 3 and a comparative group, and were then subjected to submerged cultivation and air-liquid interface cultivation using the procedures described in section A of Example 2. On the eighteenth day after starting the air-liquid interface cultivation, the liquid medium in the transwell inserts of a respective one of the test groups was removed, and the thus formed 3D cell cultures of alveolar epithelium of the experimental groups 1 to 3 were respectively infected with SARS-CoV-2 pseudovirus prepared in fresh GM medium at a multiplicity of infection (m.o.i.) of 1, 10 and 20 for 24 hours, while that of the comparative group was subjected to the same treatment except that the fresh GM medium was free from SARS-CoV-2 pseudovirus. Next, the liquid medium was removed, and the thus infected 3D cell culture of alveolar epithelium of the respective one of the test groups was washed with DPBS. Thereafter, the transwell inserts of the respective one of the test groups without GM medium added therein were placed in a 24-well plate containing fresh GM medium, and then the infected 3D cell culture of alveolar epithelium of the respective one of the test groups was subjected to air-liquid interface cultivation performed in an incubator at culture conditions set at 37° C. and 5% $CO_2$ for 3 days. At the end of the third day after starting the air-liquid interface cultivation, a portion of the infected 3D cell culture of alveolar epithelium of the respective one of the test group was subjected to immunofluorescence staining assay using the procedures described in section 1 of the General Experimental Procedures for detection of HTI-56 and HT2-280 proteins (i.e., markers of AT1 cells and AT2 cells, respectively), followed by performing preliminary observation of the presence of SARS-CoV-2 pseudovirus in each of the test groups through detection of the GFP fused to the spike protein of SARS-CoV-2 pseudovirus. Subsequently, in order to verify the presence of SARS-CoV-2 pseudovirus in the AT1 cells and AT2 cells, the thus stained 3D cell culture of alveolar epithelium in the experimental group 3 was further subjected to imaging at a higher magnification.

In addition, in order to confirm the presence of inflammation in the 3D cell culture of alveolar epithelium after the SARS-CoV-2 infection, at the end of the third day after starting the air-liquid interface cultivation, 100 μL of fresh GM medium was added to a remaining portion of the aforesaid infected 3D cell culture of alveolar epithelium of the experimental group 3 and that of the comparative group, followed by incubation for 15 minutes. After that, 100 μL of a culture supernatant obtained from the infected 3D cell culture of alveolar epithelium of the experimental group 3 and that of the comparative group were subjected to determination of interleukin 8 (IL-8) concentration therein using Invitrogen™ IL-8 Human Uncoated ELISA Kit (Manufacturer: Thermo Fisher Scientific; Catalogue No.: 88-8086), and the difference between the thus obtained IL-8 concentration of the experimental group and that of the comparative group was analyzed using two-tailed Student's t-test according to the procedures described in section 2 of the General Experimental Procedures.

Figure 10:
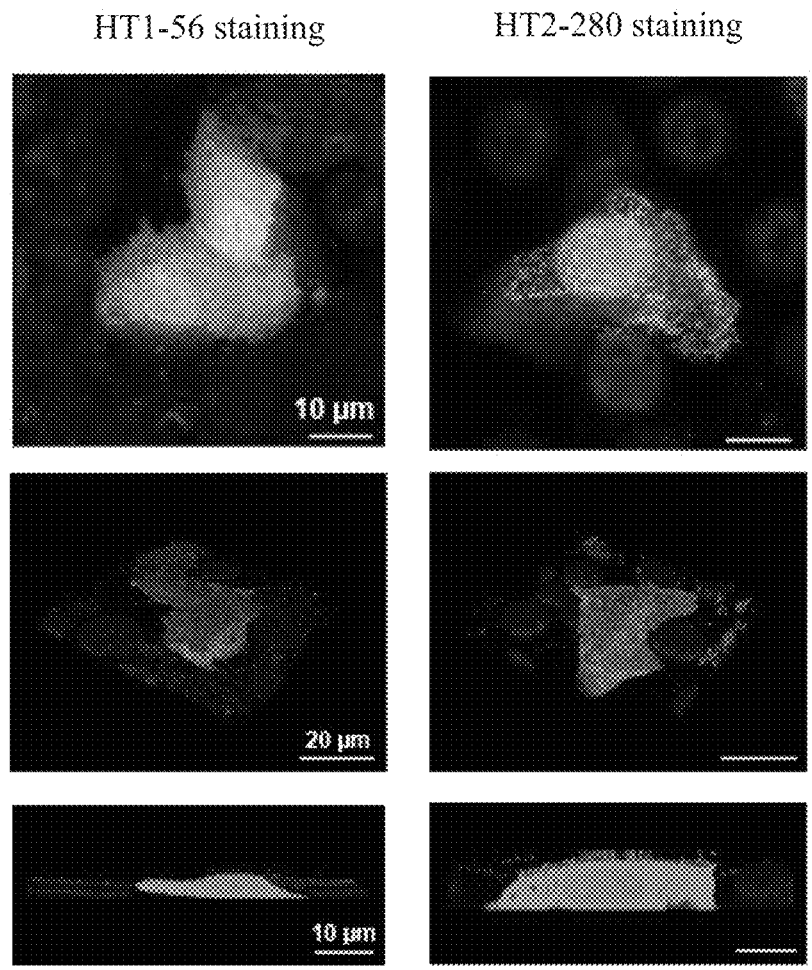
FIG. 10 shows enlarged images of the stained AT1 cells, AT2 cells, SARS-CoV-2 pseudovirus and cell nuclei of the 3D cell culture of alveolar epithelium in the experimental group 3 as shown in FIG. 9, in which the AT1 cells, AT2 cells, SARS-CoV-2 pseudovirus and cell nuclei were respectively represented by red, purple, green and blue fluorescence.

Results:

FIGS. 9 and 10 show the result of the immunofluorescence staining assay for detection of HT1-56 and HT2-280 proteins as markers of AT1 cells and AT2 cells, respectively, as well as for observing the presence of SARS-CoV-2 pseudovirus in the 3D cell culture of alveolar epithelium that was harvested at the end of the third day after starting the air-liquid interface cultivation following infection with the SARS-CoV-2 pseudovirus. As shown in FIG. 9, the SARS-CoV-2 pseudovirus represented by the green fluorescence (i.e., detection of the GFP fused to the spike protein of the SARS-CoV-2 pseudovirus) was detected in the 3D cell culture of alveolar epithelium of each of the experimental groups 1 to 3 but was absent in the comparative group, and the number of the SARS-CoV-2 pseudovirus gradually increased with the increase in m.o.i. value, indicating that the 3D cell culture of alveolar epithelium obtained using the method of the present disclosure can be infected with the SARS-CoV-2 pseudovirus.

FIG. 10 shows images of the stained AT1 cells and AT2 cells in the 3D cell culture of alveolar epithelium of the experimental group 3 which were taken at a higher magnification. As shown in FIG. 10, the SARS-CoV-2 pseudovirus represented by the green fluorescence was readily detected together with the HT1-56 and HT2-280 proteins that are respectively represented by the red and purple fluorescence, suggesting that SARS-CoV-2 pseudovirus was present both in the AT1 cells and the AT2 cells.

Figure 11:
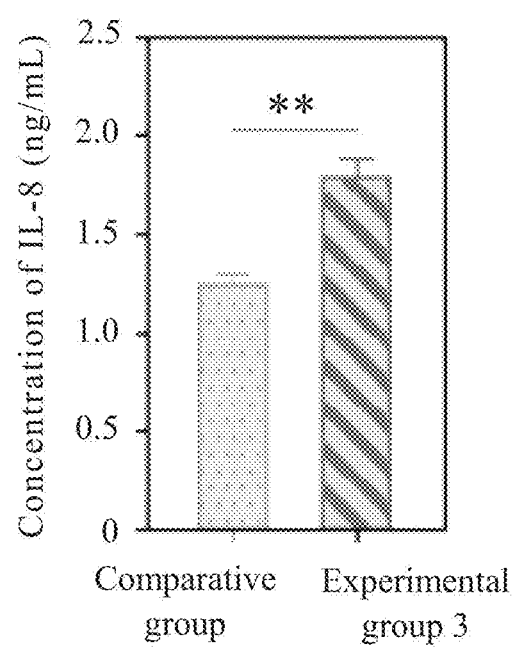
FIG. 11 is a graph showing the concentration of IL-8 in the culture supernatant of the 3D cell culture of alveolar epithelium in each of the experimental group 3 and the comparative group of Example 3, infra, in which the symbol "**" represents $p<0.01$ compared with the comparative group.

FIG. 11 shows the concentration of IL-8 in the culture supernatant of the 3D cell culture of alveolar epithelium in the experimental group 3 and that of the comparative group which were measured at the end of the third day after starting the air-liquid interface cultivation following infection with the SARS-CoV-2 pseudovirus. As shown in FIG. 11, the concentration of IL-8 in the culture supernatant of the experimental group 3 was significantly higher as compared with that of the comparative group, suggesting that inflammatory response was induced in the SARS-CoV-2 pseudovirus-infected 3D cell culture of alveolar epithelium.

C. Evaluation of Antiviral Effect of Anti-Angiotensin Converting Enzyme 2 (ACE2) Antibody on SARS-CoV-2 Pseudovirus Experimental Procedures:

The primary HPAEpiC that had been subjected to sub-culturing using the GM medium (i.e., the basal medium containing the various supplementary components but excluding the Y-27632) as described in Example 1 were divided into 2 test groups, i.e., a pathological control group and an experimental group, and were then subjected to submerged cultivation using the procedures described in section A of Example 2. On the eighteenth day after starting the submerged cultivation, the thus formed 3D cell culture of alveolar epithelium in the experimental group was subjected to pre-treatment with 20 μg/mL of anti-ACE2 antibody (Manufacturer: Abcam; Catalogue No.: ab87463) that was dissolved in a basal medium for 30 minutes, while that in the pathological control group was subjected to same treatment except that the anti-ACE2 antibody was omitted from the basal medium. After that, the liquid medium was removed, and the 3D cell culture of alveolar epithelium in a respective one of the pathological control group and the experimental group was washed with DPBS, and was then infected with the SARS-CoV-2 pseudovirus at a m.o.i. of 20. Subsequently, the infected 3D cell culture of alveolar epithelium in the respective one of the pathological control group and the experimental group was subjected to air-liquid interface cultivation using the procedures described in the abovementioned section entitled "B. Verification of SARS-CoV-2 pseudovirus infection".

At the end of the third day after starting the air-liquid interface cultivation, the 3D cell culture of alveolar epithelium of the respective one of the pathological control group and the experimental group was harvested and subjected to DAPI (4',6-diamidino-2-phenylindole) staining (i.e., staining with a marker of cell nucleus) for SARS-CoV-2 pseudovirus detection and quantification of the percentage ratio of SARS-CoV-2±cells using the procedures described in section 1 of the General Experimental Procedures.

The relative infection efficiency of the SARS-CoV-2 pseudovirus in the 3D cell culture of alveolar epithelium of the respective one of the pathological control group and the experimental group was determined by dividing the quantified percentage ratio of SARS-CoV-2$^+$ cells in the respective one of the pathological group and the experimental group with that in the pathological control group, so as to normalize the thus obtained percentage ratio of SARS-CoV-2$^+$ cells. The difference between the thus obtained relative infection efficiency of the experimental group and that of the pathological control group was analyzed using two-tailed Student's t-test according to the procedures described in section 2 of the General Experimental Procedures.

Figure 12:
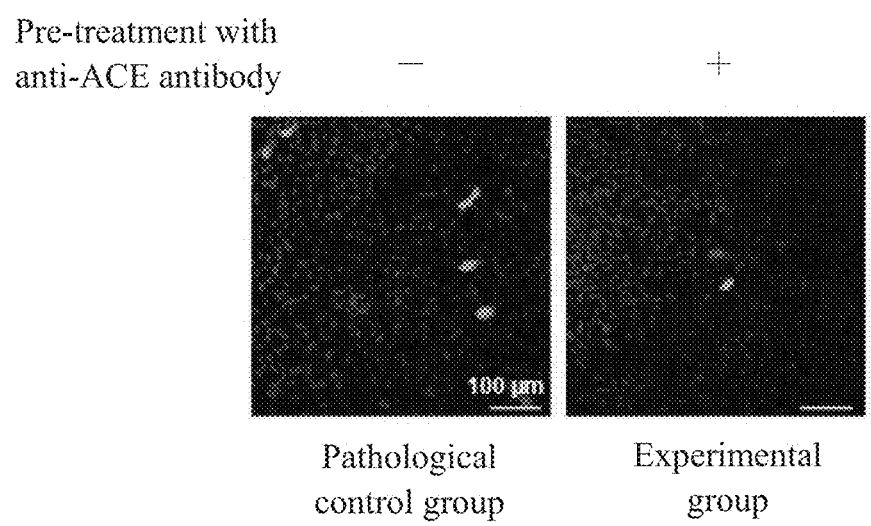
FIG. 12 shows the result of immunofluorescence staining assay for detection of SARS-CoV-2 pseudovirus in the 3D cell culture of alveolar epithelium of each of the pathological control group and the experimental group of Example 3, infra, in which the SARS-CoV-2 pseudovirus and cell nuclei were respectively represented by the green and blue fluorescence.

Results:

FIG. 12 shows the result of the immunofluorescence staining assay for detection of SARS-CoV-2$^+$ cells in the 3D cell culture of alveolar epithelium that was, prior to SARS-CoV-2 pseudovirus infection, pre-treated with anti-ACE2 antibody (i.e., the experimental group) or not pre-treated with anti-ACE2 antibody (i.e., the pathological control group). As shown in FIG. 12, in comparison with the pathological control group, the amount of the SARS-CoV-2$^+$ cells which are represented by the green fluorescence was significantly less in the experimental group.

Figure 13:
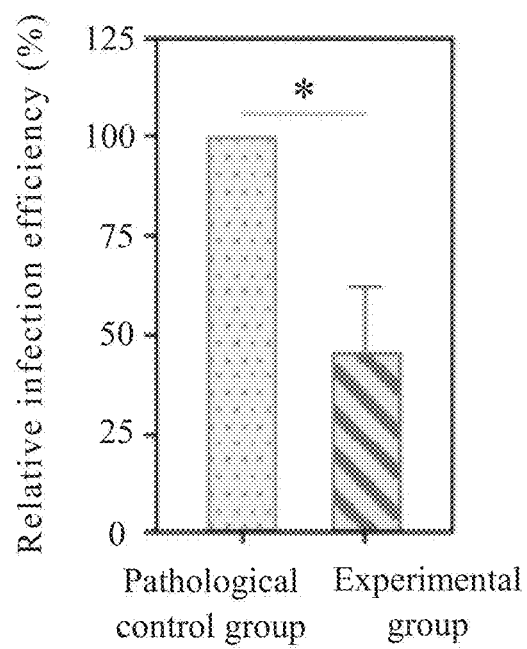
FIG. 13 is a graph showing the relative infection efficiency of the SARS-CoV-2 pseudovirus in the infected 3D cell culture of alveolar epithelium in each of the pathological control group and the experimental group of Example 3, infra, in which the symbol "*" represents $p<0.05$ compared with the pathological control group.

FIG. 13 shows the relative infection efficiency of the SARS-CoV-2 pseudovirus in the infected 3D cell culture of alveolar epithelium in each of the pathological control group and the experimental group. As shown in FIG. 13, in comparison with the pathological control group, the relative infection efficiency of the SARS-CoV-2 pseudovirus was significantly reduced in the experimental group that was subjected to the pre-treatment with anti-ACE2 antibody prior to infection with SARS-CoV-2 pseudovirus, indicating that the 3D cell culture of alveolar epithelium prepared using the method of the present disclosure can be utilized as an in vitro model of alveolar epithelium for viral infection, and hence is expected to be useful for evaluating the antiviral effects of drugs.

Taken together, these results demonstrate that the 3D cell culture of alveolar epithelium prepared using the method of the present disclosure is capable of expressing host cell proteins involved in the entry of SARS-CoV-2 into host cells and initial priming of the SARS-CoV-2 spike protein in the host cells, can be infected by SARS-CoV-2, and hence, is expected to be useful as an in vitro model of alveolar epithelium for performing research related to SARS-CoV-2 infection and screening of drugs against SARS-CoV-2.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for preparing a three-dimensional cell culture of alveolar epithelium, comprising:

subjecting primary human pulmonary alveolar epithelial cells to submerged cultivation in a first medium that includes a basal medium, a culture supplement, and a Rho kinase inhibitor, so as to obtain cultured primary human pulmonary alveolar epithelial cells;

subjecting the cultured primary human pulmonary alveolar epithelial cells to submerged cultivation in a second medium that includes the basal medium and the culture supplement, so as to obtain proliferated primary human pulmonary alveolar epithelial cells; and subjecting the proliferated primary human pulmonary alveolar epithelial cells to air-liquid interface cultivation in the second medium, so as to obtain the three-dimensional cell culture of alveolar epithelium, wherein the culture supplement includes Jagged-1 (JAG 1) peptide, human Noggin (hNoggin) protein, SB431542, human fibroblast growth factor 7 (hFGF-7), human fibroblast growth factor 10 (hFGF-10), and CHIR99021.

2. The method as claimed in claim 1, wherein the primary human pulmonary alveolar epithelial cells are subjected to the submerged cultivation in the first medium in the presence of an extracellular matrix.

3. The method as claimed in claim 2, wherein the extracellular matrix is selected from the group consisting of type I collagen, type IV collagen, gelatin, fibronectin, solubilized basement membrane matrix secreted by Engelbreth-Holm-Swarm mouse sarcoma cells growth factor reduced (GFR) basement membrane matrix, basement membrane extract, and combinations thereof.

* * * * *